(12) United States Patent
Mohiuddin

(10) Patent No.: US 7,201,525 B2
(45) Date of Patent: Apr. 10, 2007

(54) LIQUID ANTIMICROBIAL SOLUTION APPLICATOR

(75) Inventor: Mahmood Mohiuddin, Hawthorn Woods, IL (US)

(73) Assignee: Allegiance Corporation, McGaw Park, IL (US)

( * ) Notice: Subject to any disclaimer, the term of this patent is extended or adjusted under 35 U.S.C. 154(b) by 178 days.

(21) Appl. No.: 10/895,724

(22) Filed: Jul. 21, 2004

(65) Prior Publication Data

US 2006/0018701 A1    Jan. 26, 2006

(51) Int. Cl.
 B43K 5/13    (2006.01)
(52) U.S. Cl. ............ 401/134; 401/132; 222/83.5; 222/80
(58) Field of Classification Search ........ 401/132–135; 222/81, 83, 83.5, 88, 89, 192, 80; 604/200
See application file for complete search history.

(56) References Cited

U.S. PATENT DOCUMENTS

| | | |
|---|---|---|
| 351,098 A | 10/1886 | Desau |
| 715,296 A | 12/1902 | Rickey |
| 940,598 A | 11/1909 | Homine |
| 1,152,817 A | 9/1915 | Hyah |
| 1,603,565 A | 10/1926 | Voss |
| 2,022,706 A | 12/1935 | Clark |
| 2,308,215 A | 1/1943 | Stern |
| 2,524,371 A | 10/1950 | Betron et al. |
| 2,544,198 A | 3/1951 | Vosbikian et al. |
| 3,160,271 A | 12/1964 | Ritter |
| 3,261,515 A | 7/1966 | Luedtke |
| 3,548,562 A | 12/1970 | Schwartzman |
| 3,802,604 A * | 4/1974 | Morane et al. ............ 222/83 |
| 3,922,099 A | 11/1975 | Christine et al. |
| 4,415,288 A | 11/1983 | Gordon et al. |
| 4,498,796 A | 2/1985 | Gordon et al. |
| 4,881,662 A * | 11/1989 | Tallman ............ 222/81 |
| 4,896,984 A | 1/1990 | Evans |
| 4,925,327 A | 5/1990 | Bohn et al. |
| 4,927,283 A | 5/1990 | Fitjer |
| 4,966,481 A | 10/1990 | Satten et al. |
| 5,120,301 A | 6/1992 | Wu |
| 5,193,928 A | 3/1993 | Balzer et al. |
| 5,240,339 A | 8/1993 | DeForest et al. |
| 5,288,159 A | 2/1994 | Wirt |
| 5,299,877 A | 4/1994 | Birden |
| 5,308,180 A | 5/1994 | Pournoor et al. |
| 5,353,819 A | 10/1994 | Kahn et al. |
| 5,435,660 A | 7/1995 | Wirt |
| 5,454,659 A | 10/1995 | Vosbikian et al. |
| 5,509,744 A | 4/1996 | Frazier |
| 5,573,342 A | 11/1996 | Patalano |
| 5,658,084 A | 8/1997 | Wirt |

(Continued)

Primary Examiner—Huyen Le
(74) Attorney, Agent, or Firm—Michael D. Steffensmeier

(57) ABSTRACT

A solution applicator includes a container, a head and a cap. The head includes a top portion for use in applying the solution, a spike member which is used to pierce or open a membrane and at least one protrusion extending from the head. The cap includes a top portion that receives the spike member, a bottom portion that connects to the container and a middle portion that defines a circumferential channel and an axial channel. The protrusion is received within the circumferential channel and the axial channel such that the head can be moved relative to the cap in first a rotational motion and then an axial motion to open the solution container.

29 Claims, 14 Drawing Sheets

U.S. PATENT DOCUMENTS

| | | |
|---|---|---|
| 5,769,552 A | 6/1998 | Kelley et al. |
| 5,791,801 A | 8/1998 | Miller |
| 5,891,129 A * | 4/1999 | Daubert et al. .............. 604/411 |
| 5,988,923 A | 11/1999 | Arai |
| 6,164,495 A * | 12/2000 | Manesis ..................... 222/129 |
| 6,371,675 B1 | 4/2002 | Hoang et al. |
| 6,412,997 B2 | 7/2002 | Berke et al. |
| 6,422,778 B2 | 7/2002 | Baumann et al. |
| 6,488,665 B1 | 12/2002 | Severin et al. |
| 6,491,463 B1 | 12/2002 | Richard |
| 6,523,550 B2 | 2/2003 | McCormick |
| 6,533,484 B1 | 3/2003 | Osei et al. |
| 6,536,970 B2 | 3/2003 | Hauser et al. |
| 6,550,996 B1 | 4/2003 | Rayfield |
| 2002/0018687 A1 | 2/2002 | Owings |
| 2002/0076255 A1 | 6/2002 | Hoang et al. |
| 2003/0049069 A1 | 3/2003 | Osei et al. |

* cited by examiner

LIQUID ANTIMICROBIAL SOLUTION APPLICATOR

I. BACKGROUND OF THE INVENTION

A. Field of Invention

The present invention generally relates to solution applicators and, more specifically, to solution applicators for applying antimicrobial solution to skin before surgery.

B. Description of the Related Art

Antiseptic preparation of patients for surgery typically includes applying antimicrobial solution to the patient's skin and scrubbing the affected area. There are a number of ways that these antimicrobial solutions are applied from the basic method of dipping a sponge or piece of cotton in an open dish of antimicrobial solution and applying the solution to the patient's skin to more complex, hand-held solution applicators.

There are a number of solution applicators that use spikes and other sharp members that puncture a cartridge or container that contains antimicrobial solution. In many of these types of solution applicators, the cartridge or container is moved longitudinally relative to the spike which then punctures the container to let the solution flow from the container to a sponge on the end of the applicator. These types of solution applicators can rupture during shipping, if the applicator is dropped or sufficient pressure is exerted onto one end of the applicators to thereby force the spike into the solution container, which can inadvertently or accidentally rupture the container and cause the solution to flow out of the container. Some examples of solution applicators using spikes are U.S. Pat. Nos. 4,415,288; 4,498,796; 5,120,301; and 5,769,552.

FIGS. 1 and 2 show a current design used by the owner of this patent. The solution applicator 1 has three major components: a container 2, a head 3, and a cap 4. Preferably a foam sponge 5 is attached to the top of the head 3. The container 2 is filled with a solution and then sealed with a membrane 9 such as an aluminum foil type membrane. The membrane 9 sealed container 2 is then fitted with the cap 4 and the head 3 is then placed over the cap 4. The head 3 includes a sharp spike feature (not shown). To activate the solution applicator, the spike feature in the head 3 is pushed into the container 2. The spike feature punctures the membrane 9 and allows the solution to flow over the patient's skin for use in, for example, preparing a patient prior to surgery.

The solution applicator 1 as just described works well for its intended purpose. However, one problem that has occurred is leaking of solution. In order to minimize leaking a compressible washer 6, an absorbent washer 7 and a clip 8 were added to the solution applicator 1. The clip 8 prevents inadvertent activation of the solution applicator 1 because the head 3 cannot be pushed down such that the spike feature contacts the membrane 9 unless the clip 8 is first removed. The absorbent washer 7 absorbs solution that may leak out. The compressible washer 6 puts uniform pressure over the membrane seal and minimizes leakage at the membrane/container interface.

There is a need for a novel solution applicator that will not easily break during shipment, when dropped, or inadvertently by a user prior to desired use of the solution applicator. The present invention meets these needs.

II. SUMMARY OF THE INVENTION

According to one aspect of this invention a solution applicator includes a container, a head, and a cap. The container includes a first portion defining an opening. The head includes a top portion for use in applying a solution, a bottom portion having a protrusion extending from the bottom portion, a spike member, and an opening within the head that permits solution to travel through the spike member to the top portion of the head. The cap includes a top portion that receives the spike member, a bottom portion that selectively connects to the first portion of the container, and a mid-portion that is received within the bottom portion of the head. The mid-portion of the cap defines at least a first circumferential channel and at least a first axial channel. The first circumferential channel receives the protrusion and permits the head to rotate relative to the cap. The first axial channel also receives the protrusion and permits the head to move axially relative to the cap.

According to another aspect of this invention, in the preferred embodiment the mid-portion of the cap includes first, second and third discs positioned substantially perpendicular to the axis of the top portion of the cap. The first and second discs define the first circumferential channel.

According to another aspect of this invention, the mid-portion of the cap also includes first and second walls positioned substantially perpendicular to the first and second discs of the cap. The first and second walls define the first axial channel.

According to still another aspect of this invention, a method of dispensing a solution includes the following steps:
(1) providing a solution applicator that includes a container, a head that has a spike member and a protrusion, and a cap that defines a first circumferential channel and a first axial channel;
(2) rotating the head relative to the cap so that the protrusion moves within the first circumferential channel;
(3) moving the head axially relative to the cap so that the protrusion moves within the first axial channel; and,
(4) extending the spike member through the membrane into the container.

According to another aspect of this invention, ramps are provided to limit the rotation of the head within the axial channel and also to limit the movement of the protrusion within the circumferential channel.

According to yet another aspect of this invention, a method of assembling a solution applicator and dispensing a solution includes the following steps:
(1) providing a solution applicator that includes a container, a head having a spike member and a cap;
(2) attaching a bottom portion of the cap to the container;
(3) placing the head onto the cap such that the cap receives the spike member and such that the cap is received within the head;
(4) rotating the head relative to the cap to a first position;
(5) moving the head axially relative to the cap to a second position for purposes of assembly;
(6) rotating the head relative to the cap to a third position;
(7) moving the head axially relative to the cap to a fourth position for purposes of applying the solution;
(8) extending the spike member into the container.

According to one embodiment of this invention, the membrane used to seal the solution within the container is first attached to a rim in the cap and then held against the container once the cap is attached to the container.

One advantage of this invention is that the assembly and directions of use are easier than currently known solution applicators.

Another advantage of this invention is that it provides reliable activation with minimal leakage.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein.

IV. DESCRIPTION OF THE PREFERRED EMBODIMENT(S)

Figure 1:
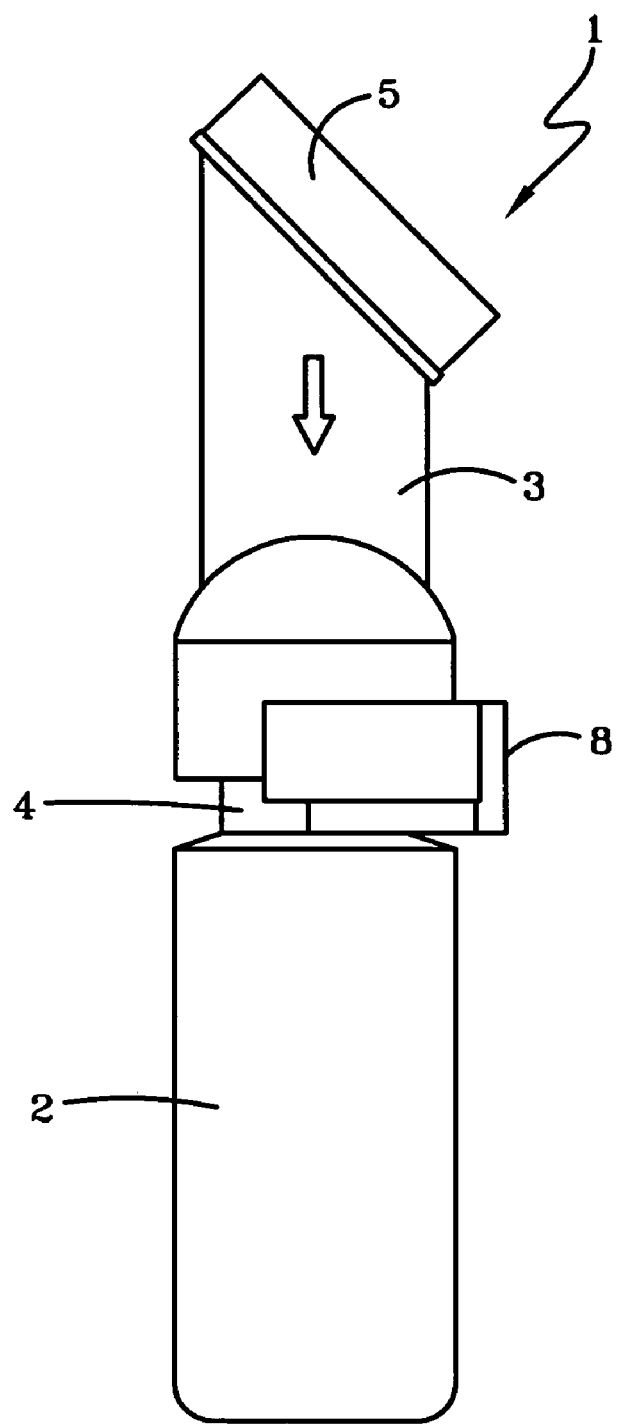
FIG. 1 is a side view of a prior art solution applicator shown assembled.
Figure 2:
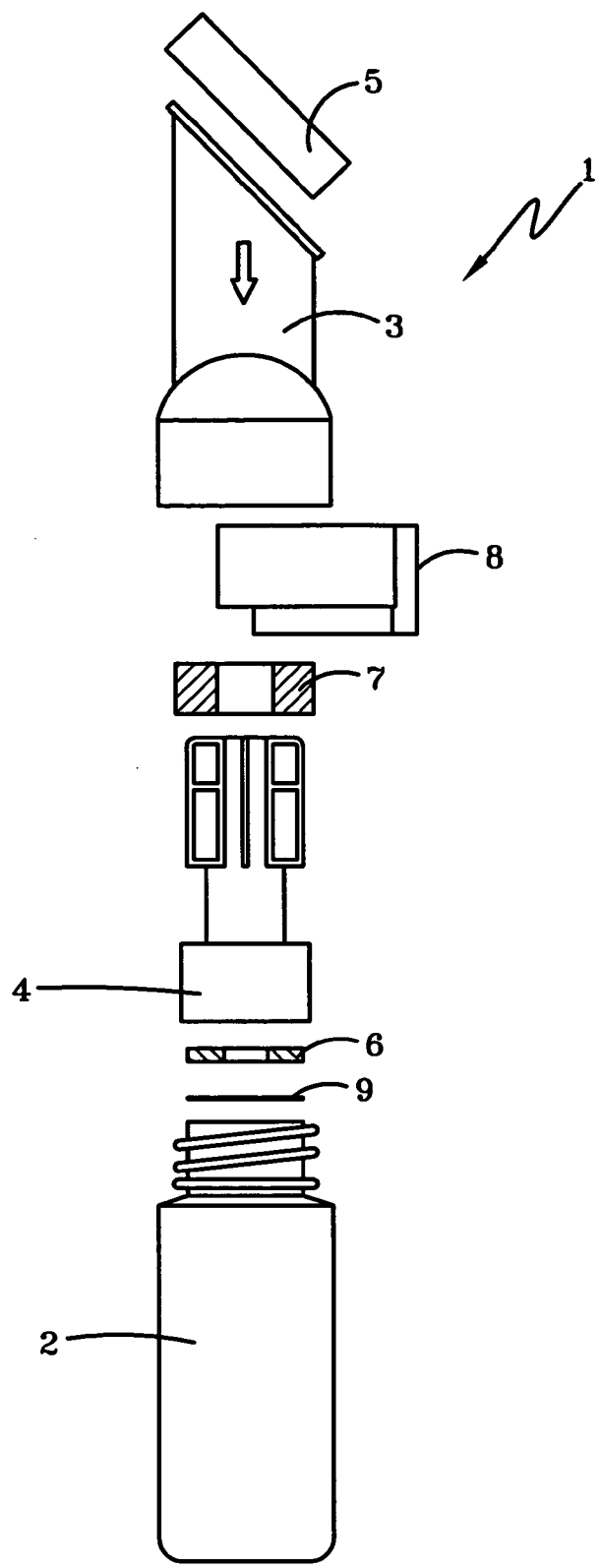
FIG. 2 is an exploded view of the prior art solution applicator of FIG. 1.
Figure 3:
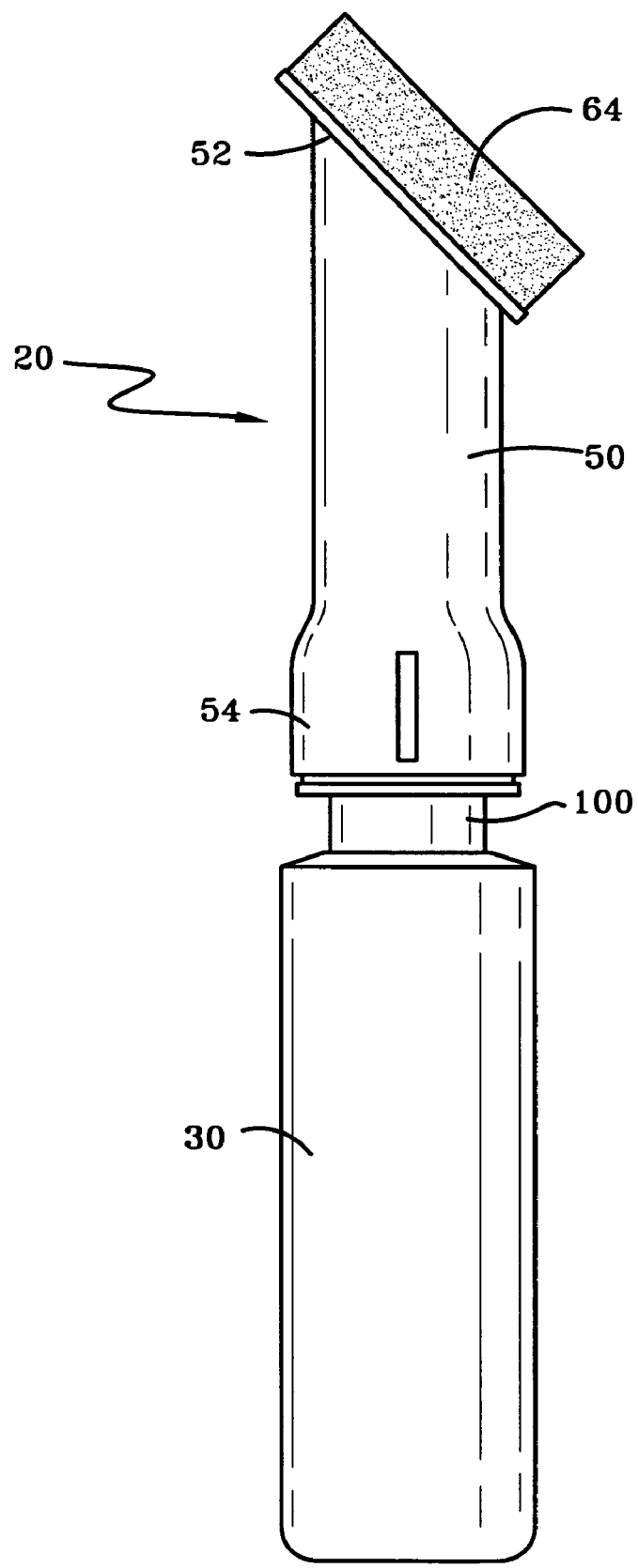
FIG. 3 is a perspective side view of the solution applicator according to this invention.
Figure 4:
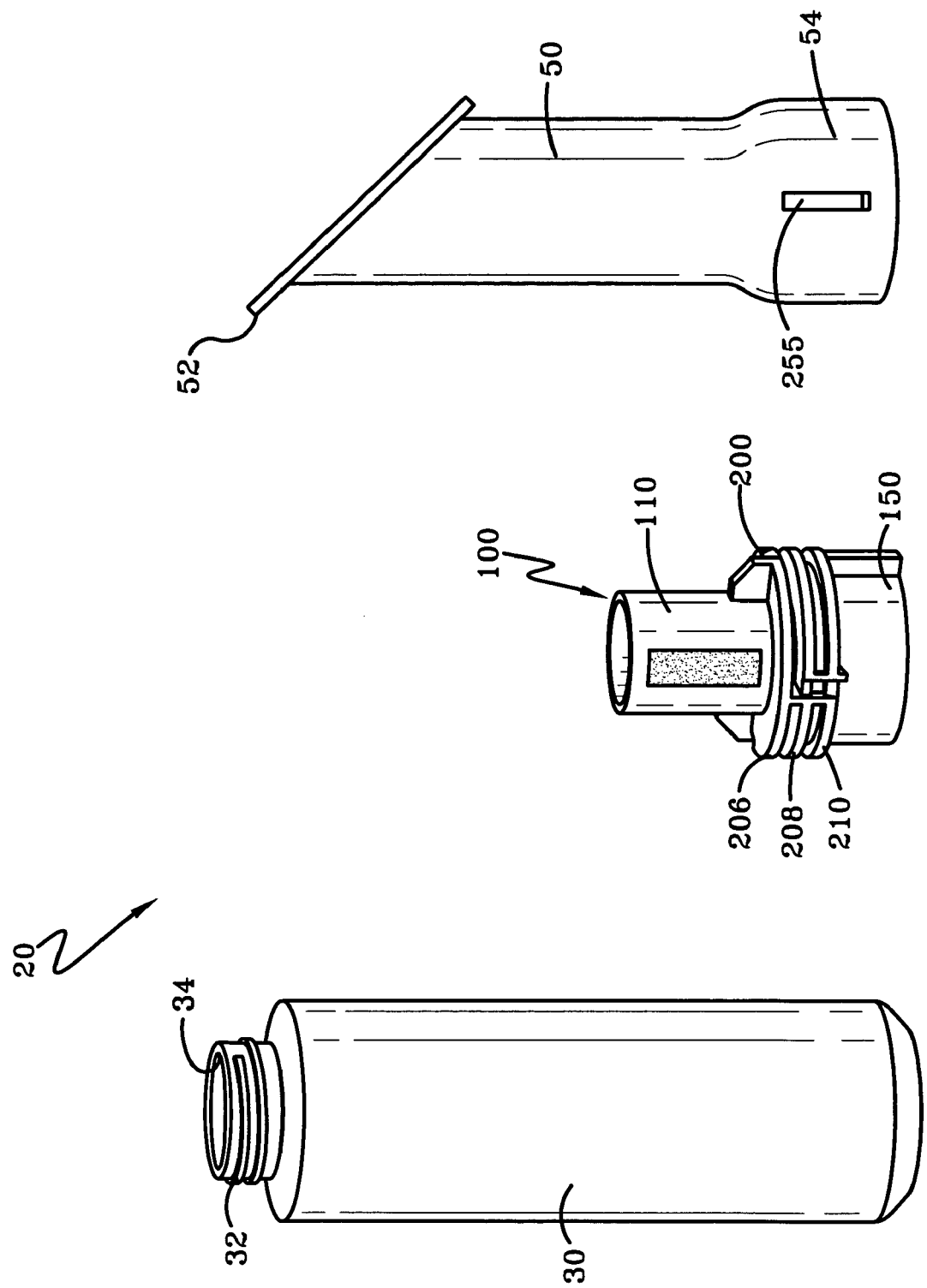
FIG. 4 shows the three main components of the solution applicator shown in FIG. 3 disassembled.

Referring now to the drawings wherein the showings are for purposes of illustrating the preferred embodiment only and not for purposes of limiting the same, FIGS. 3–4 show a solution applicator 20 according to this invention. The solution applicator 20 has three primary components: a container 30, a cap 100 and a head 50. While these components may be formed of any material chosen with sound engineering judgment, in the preferred embodiment they are formed of plastic. The container 30 includes a first portion 32 that defines an opening 34. The container 30 is used to hold and store a solution such as, for example, an antimicrobial solution, that is to be applied to the patient. Preferably, the first portion 32 of the container 30 includes threads, as shown, to receive the cap 100 as will be described further below.

Figure 9:
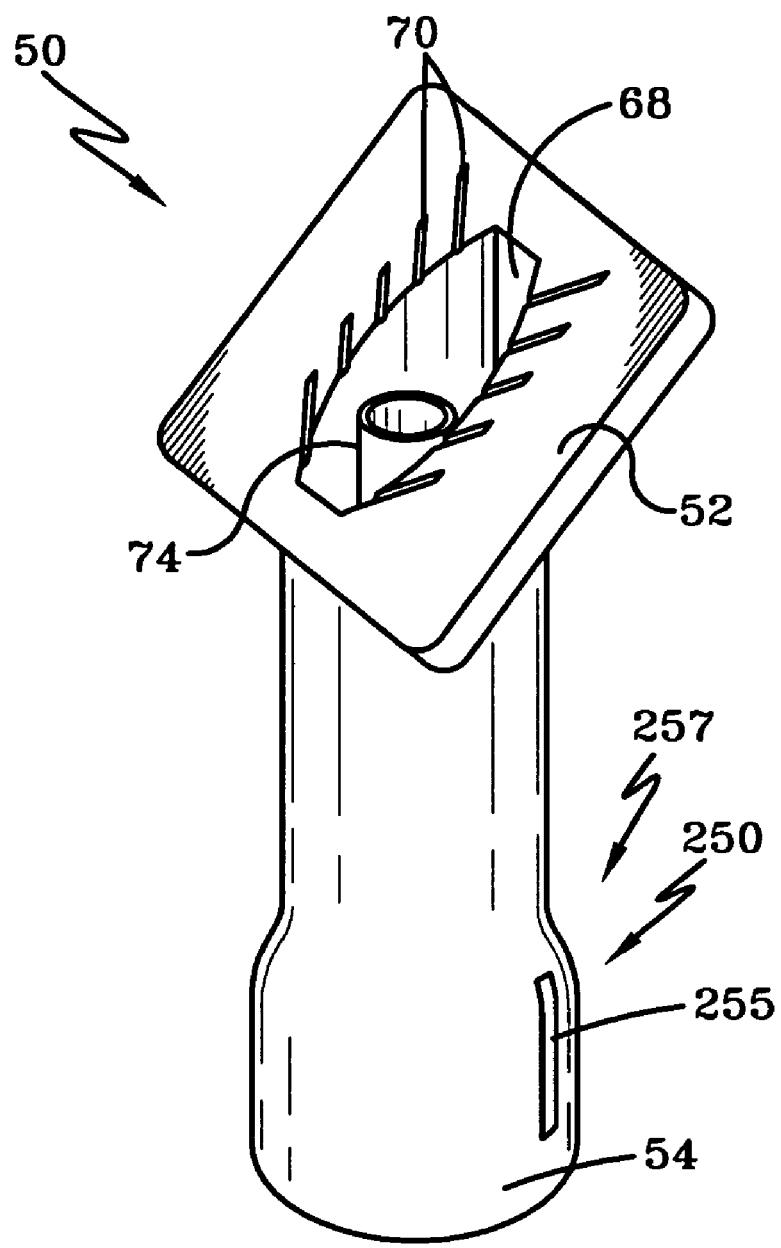
FIG. 9 is a perspective top view of the head showing the grooves used to direct solution into the reservoir.
Figure 10:
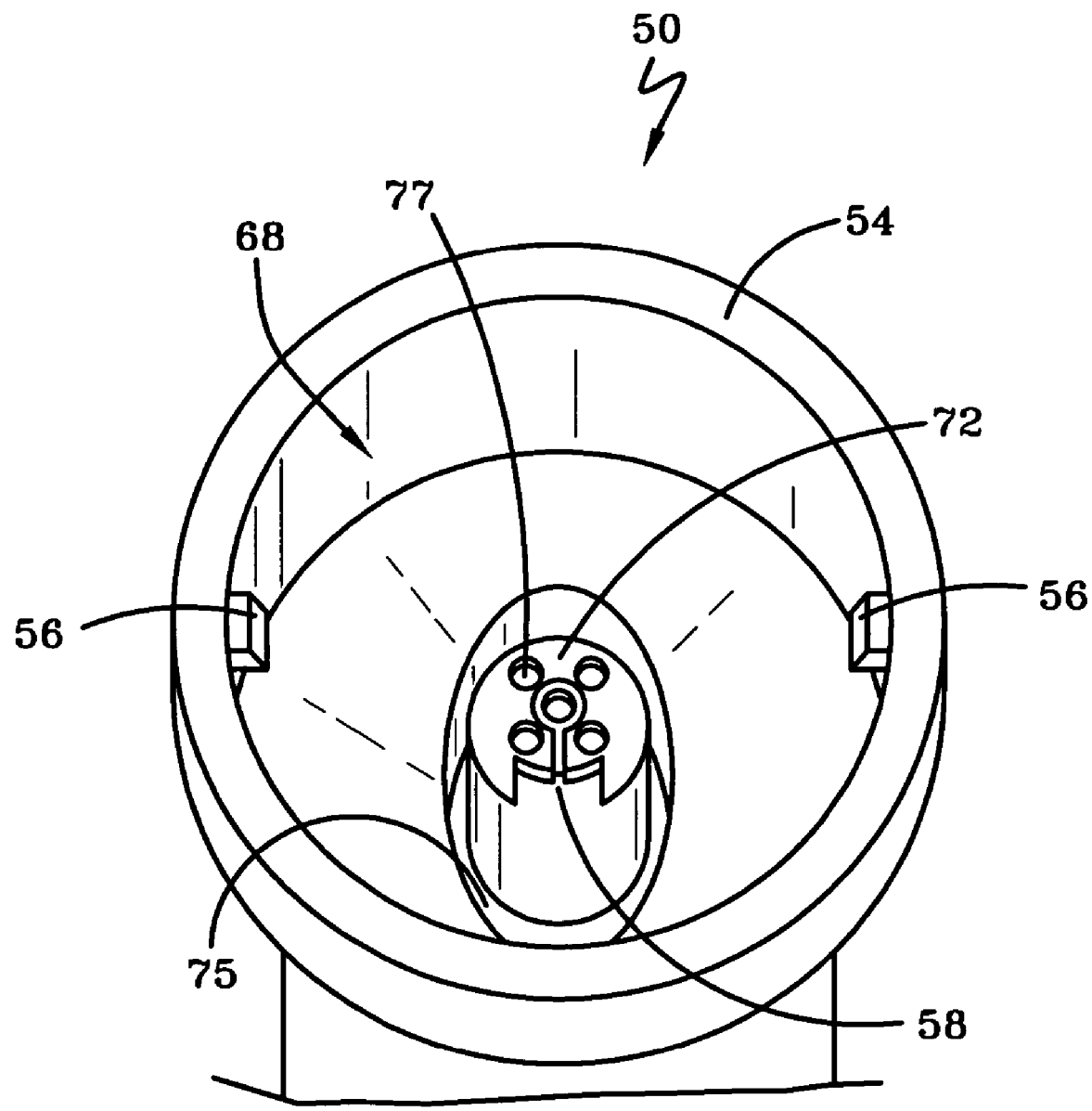
FIG. 10 is a bottom view of the head showing the protrusions used to engage the channels formed in the cap.
Figure 13:
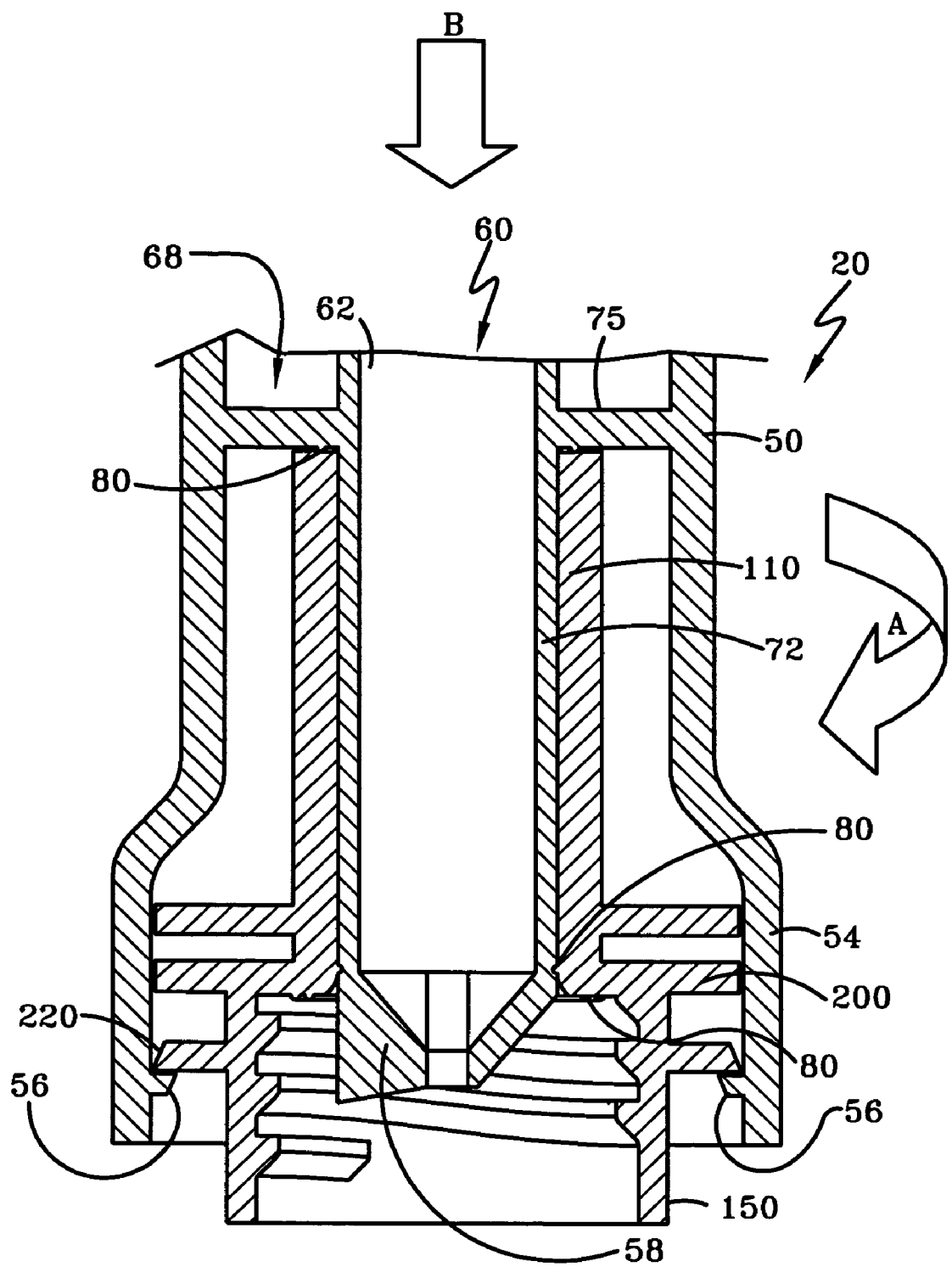
FIG. 13 is a cut away sectional view similar to FIG. 11 but showing the spike member after it pierced the membrane.

With reference now to FIGS. 3–4, 9–11 and 13, the head 50 will be described. Preferably, the head 50 includes a top portion 52 that is used in applying the solution and a bottom portion 54. As seen in FIGS. 10 and 13, at least a first protrusion 56 is attached to and extending from the bottom portion of the head 50. In the preferred embodiment, two protrusions 56 are used as shown, however, this invention would work with a single protrusion or multiple protrusions. It should also be noted that while in the preferred embodiment the protrusions 56 extend inwardly from an inside surface of the head 50, other orientations would work equally well with this invention. This could be a protrusion extending from cap 100 and being operatively connected to head 50. The bottom portion 54 of the head 50 has an inside diameter sufficient to receive a later to be described midportion 200 of the cap 100. In the preferred embodiment, the bottom portion 54 has at least one slot 255 (FIG. 9) for use in aligning the head 50 with the cap 100 as will be discussed further below. Most preferably there are two slots 255 on opposite sides of the bottom portion 54. The head 50 includes a passageway 60 for use in communicating solution from one end of the head 50 to the other. In the preferred embodiment, this passageway 60 includes a spike tube 72 that extends downwardly and an upper tube 74 that extends upwardly. Most preferably, the spike tube 72 and the upper tube 74 are coaxially aligned, as shown. Spike tube 72 and upper tube 74 may be integrally formed together.

With continuing reference to FIGS. 3–4, 9–11 and 13, the spike tube 72 and upper tube 74 are attached to an inner surface of the head 50 with a ring 75 as shown in FIGS. 10 and 13. In the preferred embodiment, the ring 75 creates a fluid seal with the inner surface of the head 50 such that the upper tube 74, the inner surface of the top portion 52 of the head 50, and the ring 75 form a solution holding reservoir 68. The reservoir 68 can be used to collect solution that may not be applied to the patient. The reservoir 68 also prevents leakage of solution, particularly when the solution applicator 20 is in a vertical orientation such as when sitting upright on a table or while scrubbing a raised patient's arm or leg. As seen in FIG. 3, a foam sponge 64 is preferably attached to the top portion 52 of the head 50. This foam sponge 64 is used to apply the solution to the patient in a manner well-known in the art. In the preferred embodiment, the top portion 52 has an upper surface with a plurality of grooves 70, best seen in FIG. 9, that permit solution that is not applied to flow from the foam sponge 64 into the reservoir 68. This greatly reduces accidental spillage of the solution.

Still referring to FIGS. 3–4, 9–11 and 13, preferably the spike tube 72 has a spike member 58 attached to or integrally formed with its lowest end. It should also be noted that the end of the spike tube 72 includes at least one and preferably several holes or openings 77 seen best in FIG. 10. These holes 77 along with the spike tube 72, the upper tube 74, and the opening 62 at the top of the upper tube 74 all together form a continuous path such that solution can be communicated from the holes 77 through the spike tube 72 and then to the foam sponge 64 when the solution applicator 20 is turned upside down for application purposes. It should be noted, however, that the solution is not released from the container 30 even when the solution applicator 20 is turned upside down until a membrane 66 that seals the solution within the container 30 (shown in FIG. 7) is first pierced or broken open. Piercing the membrane 66 thus opens the seal between the cap 100 and the container 30 so that the solution can flow out of the container 30. The membrane 66 is pierced by the insertion of the spike member 58 into and through the membrane 66. This procedure will be discussed further below.

With reference now to FIGS. 4–8, the cap 100 will be described. Preferably the cap 100 includes a top portion 110, a bottom portion 150 and a mid-portion 200. The cap 100 also has an opening 228 that extends throughout the cap 100 and is used to communicate solution from the container 30 to the head 50. The top portion 110 receives the spike tube 72 described earlier in a manner that permits the spike tube 72 to move axially within the top portion 110 of the cap. In the preferred embodiment, the spike tube 72 is received within the top portion 110 of the cap 100 with an interference fit. This provides for proper use of the solution applicator 20 but minimizes leakage. The bottom portion 150 selectively connects to the first portion 32 of the container 30. Preferably the bottom portion 150 includes threads 152 (shown in FIG. 8) that are received for connection by the threads on the top portion 110 of the container 30 in a manner well-known in the art. The mid-portion 200 of the cap 100 preferably is circular in cross-section and forms the widest portion of the cap 100. In the preferred embodiment, the mid-portion 200 provides at least a first circumferential channel 202 and at least a first axial channel 204. These channels 202, 204 receive the protrusions 56 in the head 50 and thereby permit the head 50, when the protrusions 56 are in a circumferential channel, to rotate relative to the cap 100 and also permit the head 50, when the protrusions 56 are in an axial channel, to move axially relative to the cap 100.

With continuing reference to FIGS. 4–8, the mid-portion 200 of the cap 100 includes first, second and third discs 206, 208, 210. Preferably, the first, second and third discs 206, 208, 210 are positioned substantially perpendicular to the axis 112 of the top portion 110 of the cap 100, as shown. The first and second discs 206, 208 define a first circumferential channel 202. Preferably, a circumferential channel 202 is defined on each side of the mid-portion 200 (shown in FIG. 11) and each channel 202 simultaneously receives a protrusion 56. It is also preferred that the mid-portion 200 of the cap 100 include first, second, third and fourth walls 212, 214, 216, 218. As seen best in FIG. 6, the first and second walls 212, 214 define a first axial channel 204. While only one first axial channel 204 is shown, preferably there is a similar axial channel on the opposite side of the cap 100. These axial channels 204 also simultaneously receive the protrusions 56 in the head 50.

Figure 5:
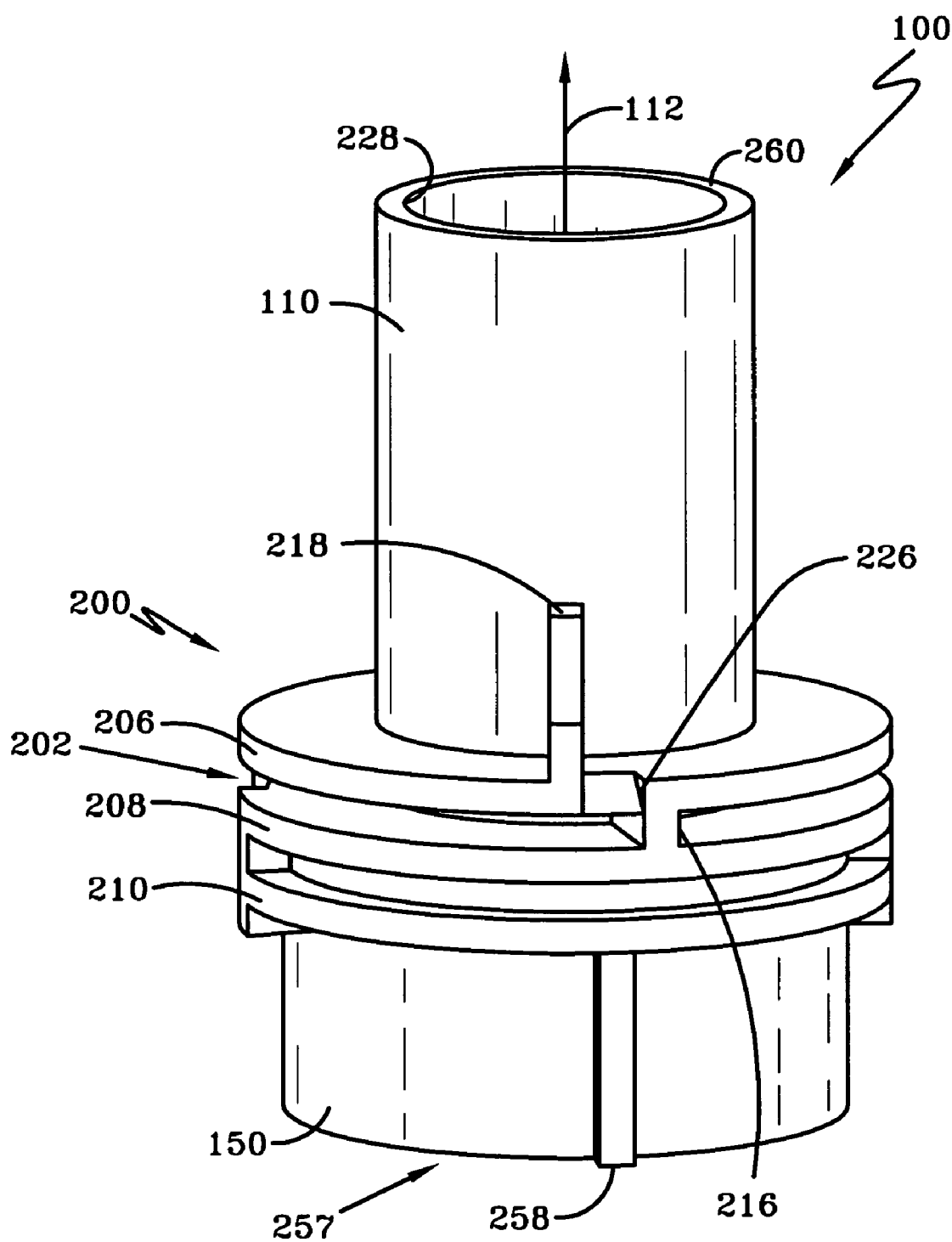
FIG. 5 is a side perspective view of the cap showing the circumferential channel.
Figure 6:
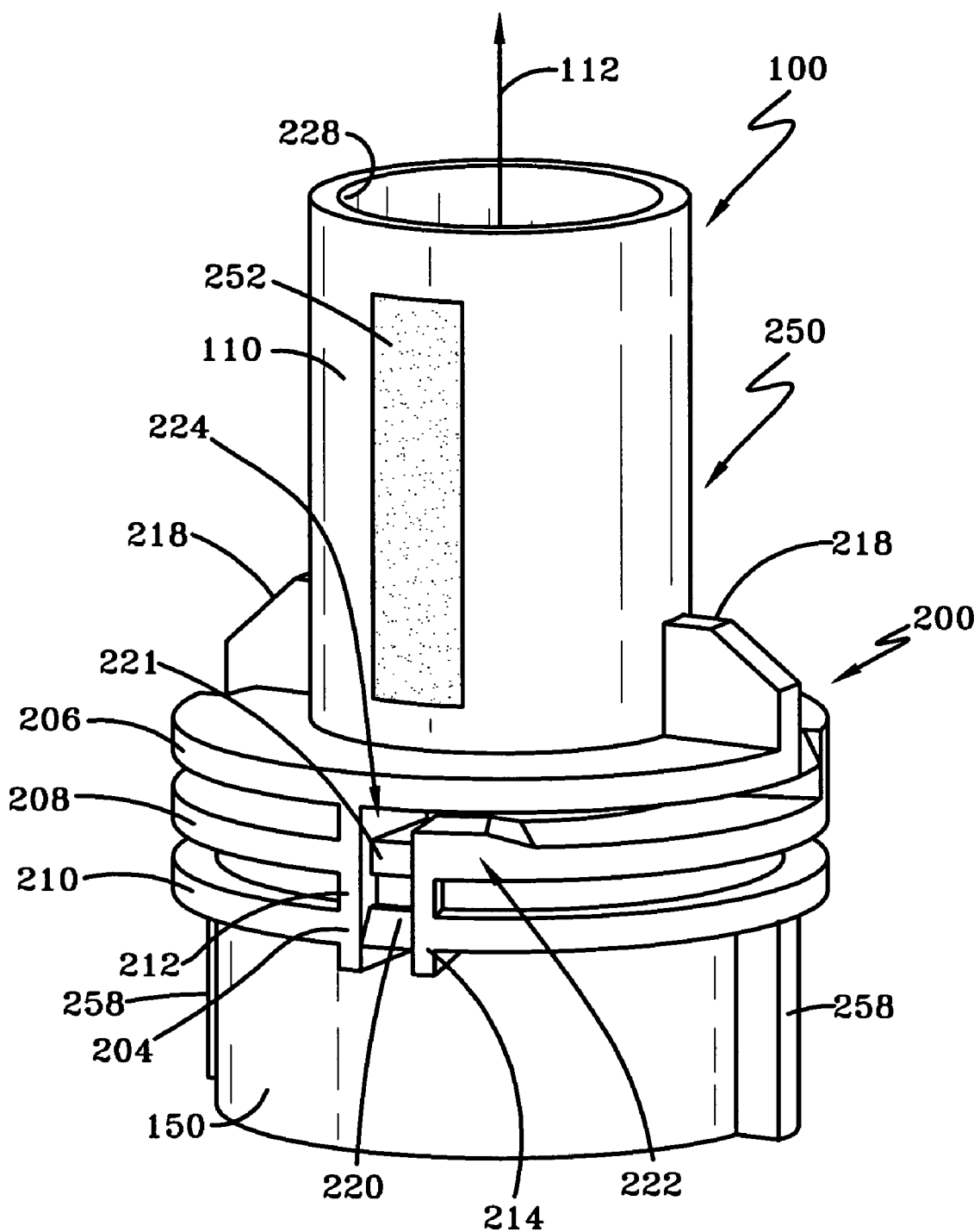
FIG. 6 is a side perspective view of the cap similar to that shown in FIG. 5 but rotated to show the axial channel.

Still referring to FIGS. 4–8, in the preferred embodiment, the motion of the protrusions 56 within the various channels 202, 204 is limited. The purpose for the motion limits is to help guide the user in operating the solution applicator 20 and also to prevent inadvertent activation of the solution applicator 20. Rotational limits are provided with the use of the third and fourth walls 216, 218. The third wall 216 is positioned within the first circumferential channel 202 and the fourth wall 218 is positioned on an upper surface of the first disc 206. While the walls 212, 214, 216, 218 provide an absolute stop to the rotational movement of the head 50 relative to the cap 100, in the preferred embodiment, another form of limitation is provided in the form of a circumferential ramp 222 as shown in FIG. 6. This ramp 222 can be formed in either the first or the second discs 206, 208, but should extend into the first circumferential channel 202 as shown. The purpose of the circumferential ramp 222 is to make it slightly more difficult to rotate the protrusion 56 within the first circumferential channel 202. This serves the purpose of preventing inadvertent rotation of the head 50 relative to the cap 100. This ramp 222 also provides a tamper proof feature because a purchaser can tell if the head 50 has been rotated beyond the ramp 222. Nonetheless, it is relatively easy for the user to rotate the head 50 through the ramp 222 when it is desired to do so. Preferably, as shown in FIG. 6, the first circumferential ramp 222 is positioned at the intersection 224 of the first circumferential channel 202 and the first axial channel 204. In this way, the rotation limit applies where most needed, that is, just prior to positioning the head 50 relative to the cap 100 in a manner where the membrane 66 can be pierced with relative axial movement.

With continuing reference to FIGS. 4–8, in the preferred embodiment there are also motion limits provided to the axial movement of the head 50 relative to the cap 100. Most preferably, these limits are created using a different type of ramp. More specifically, as seen in FIG. 6, a first axial ramp 220 is formed at an outer edge of the third disc 210. This ramp 220 is preferably formed by creating a wedge shape at the edge of the disc as shown. Most preferably, just above the first axial ramp 220 the edge of the second disc 208 has a reduced diameter portion 221 formed within the first axial channel 204. This makes it easy for the head 50 to be moved axially relative to the cap 100. The ramp 220, however, requires slightly more force by the user in order to prevent inadvertent activation of the solution applicator 20. Nonetheless, it is easy for the user to move the head 50 axially relative to the cap 100 when it is desired to pierce the membrane 66 and release the solution within the container 30. If it is desired to slightly increase the force required to overcome the axial movement limit, an additional axial ramp could be formed on the edge of the second disc 208 similar to the axial ramp 220 formed on the edge of the third disc 210. The axial ramp 220 may also be used to prevent inadvertent activation if the head 50 has been accidentally rotated. As the head moves axially through its full range of motion, the protrusions 56 move against the axial ramps 220 and lock underneath the axial ramps 220. This locked condition prevents the head 50 from returning to its previous position. While in this locked condition, pressure on the container 30 such as might be applied by the user, is insufficient to push the head 50 forward. Thus, the locked condition prevents the solution from leaking out between the container 30 and the head 50.

Figure 11:
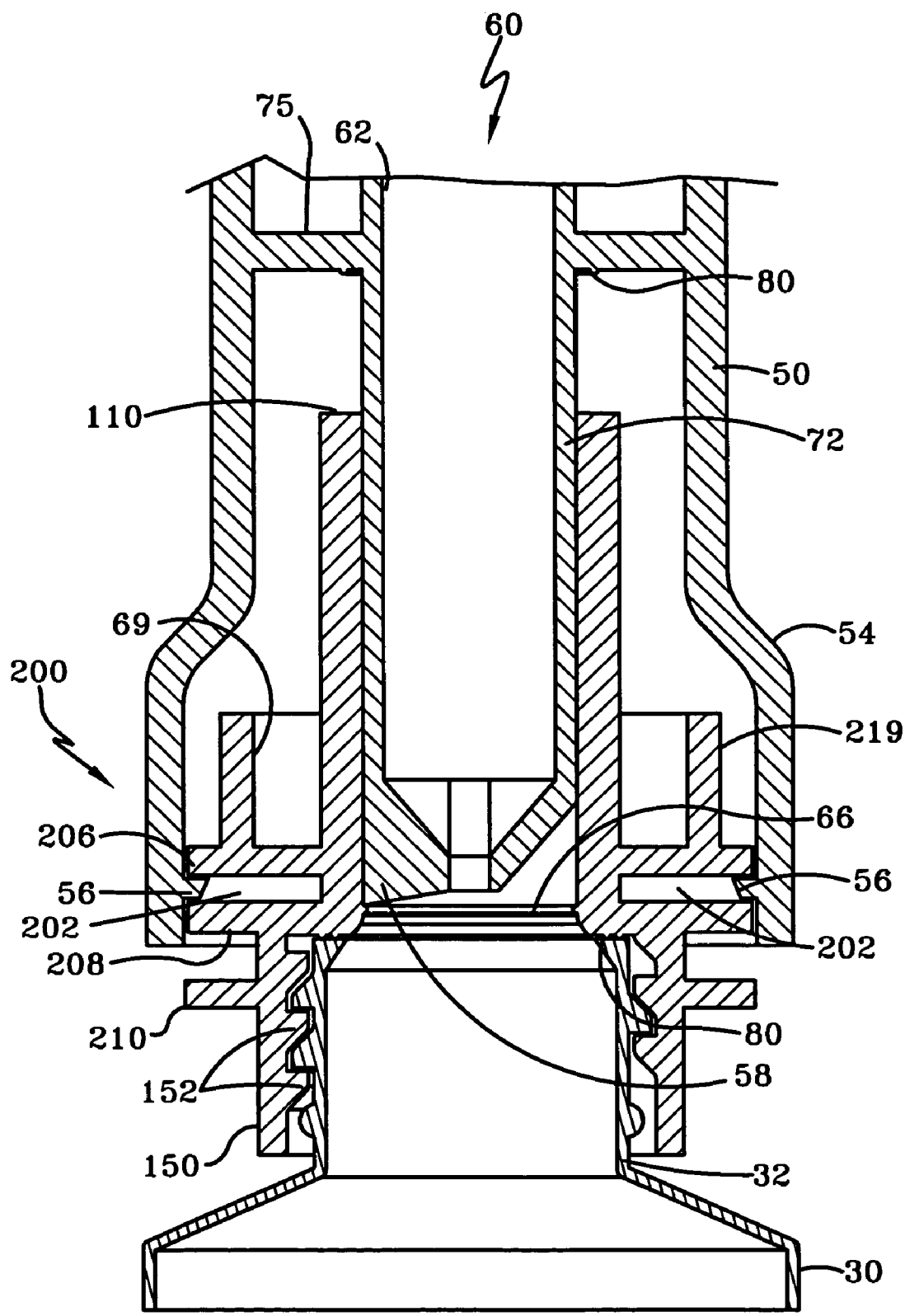
FIG. 11 is a cut away sectional view of the solution applicator showing the spike member in a position prior to its piercing of the membrane.

With reference now to FIG. 11, another wall 219 may optionally be provided to extend from the top surface of the top disc 206. The inner surface of the wall 219, the top surface of the top disc 206 and the outer surface of the top portion 110 of the cap 100 combine to form another solution holding reservoir 69. This reservoir 69 can be used to collect solution that may not be applied to the patient.

With reference now to FIGS. 4, 6 and 9, in the preferred embodiment an alignment indicator 250 is provided to assist in the use of the solution applicator 20. The preferred alignment indicator 250 provides a visual indication that the head 50 is positioned relative to the cap 100 in a manner where the membrane 66 can be pierced with relative axial movement only. More specifically, the alignment indicator 250 provides a visual indication that the protrusion 56 in the head 50 is positioned at the intersection 224 of the first circumferential channel 202 and the first axial channel 204. Though the alignment indicator 250 can be of any type chosen with sound engineering judgment, the preferred alignment indicator 250 includes the previously noted slot 255 in the head and a marking 252 positioned on the cap 100 axially above the intersection 224, as shown in FIG. 6. Preferably the marking 252 is of a color, such as red, or combination of colors that are distinct and easily visually recognizable when compared to the neighboring surface of the cap 100. Most preferably, a separate marking 252 is provided on each side of the cap 100. When the solution applicator 10 is assembled, the markings 252 can only be seen by the user when the slots 255 in the head 50 are positioned in alignment with the markings 252.

Figure 7:
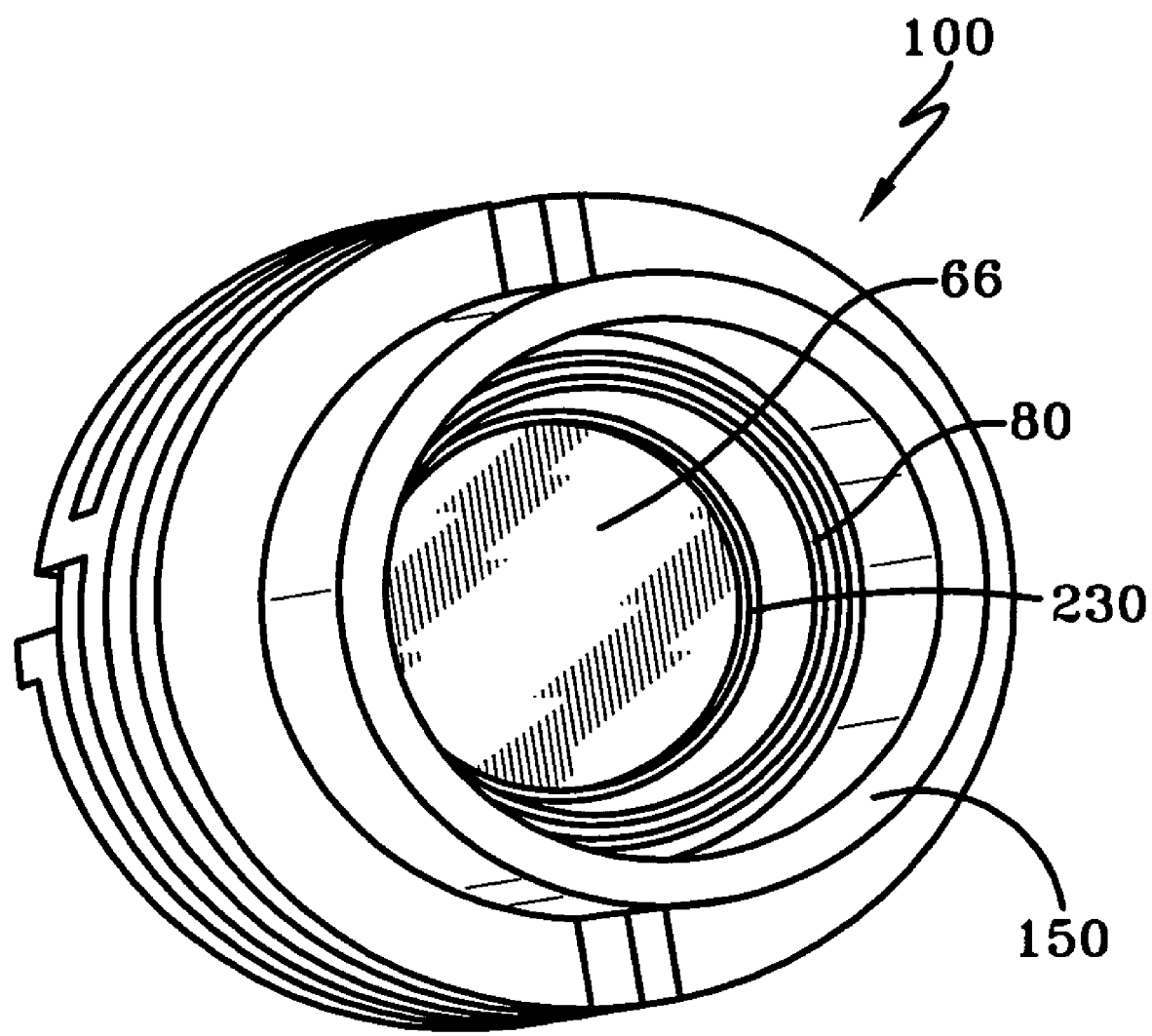
FIG. 7 is a perspective bottom view of the cap.
Figure 8:
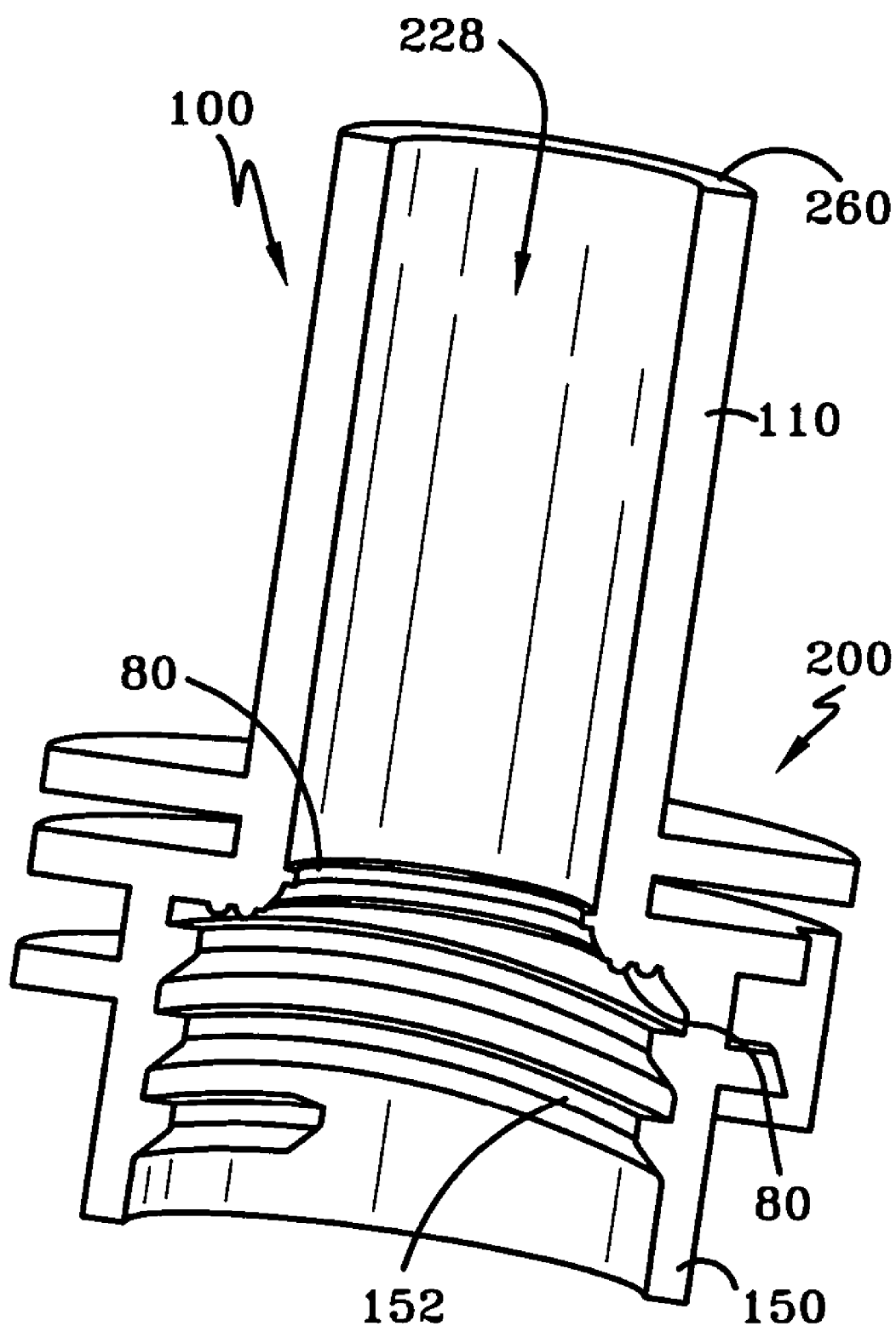
FIG. 8 is a cut away sectional view of the cap showing the internal threads used to attach the cap to the container.

With reference now to FIGS. 4 and 7–8, there are two alternate embodiments provided for holding the membrane 66 into a sealing relationship with the container 30. In one embodiment, the membrane 66 is placed onto the upper surface of the first portion 32 of the container 30 to seal the opening 34 and thus seal the solution within the container 30. Preferably, this placement of the membrane 66 onto the container 30 is done with an induction sealing process as is known by those skilled in the art. In another embodiment, the membrane 66 is first connected to the cap 100. For this embodiment, the cap 100 preferably includes a rim portion 230. The membrane 66 is positioned against this rim portion 230 and held in sealing relationship with the container 30 when the cap 100 is attached to the container 30.

Figure 14:
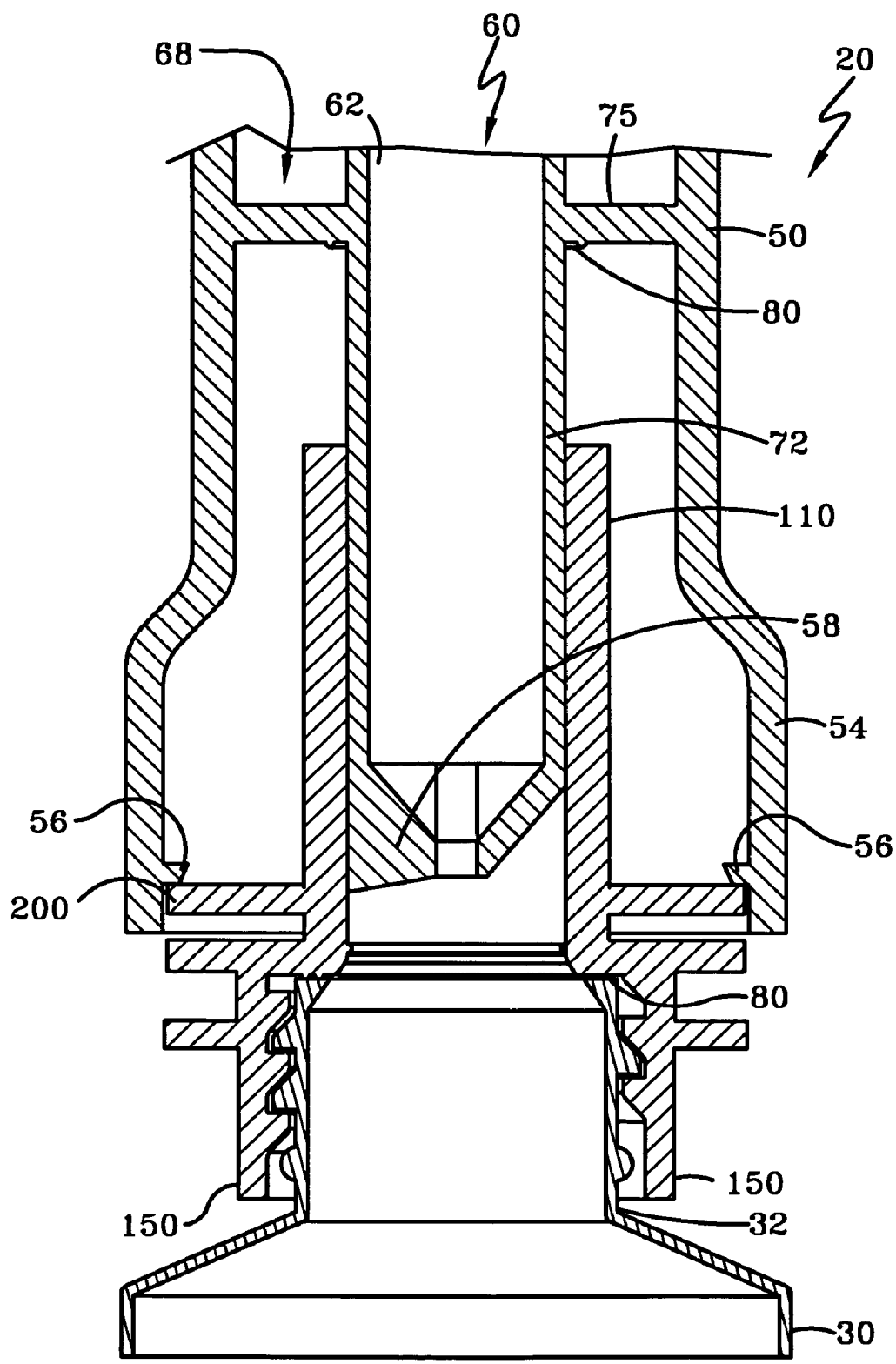
FIG. 14 is a side cut away view of the solution applicator shown during an assembly position.

With reference now to FIGS. 8, 11, and 13–14, in the preferred embodiment, a plurality of sealing ribs 80 are provided to minimize leakage of the solution when the solution applicator 20 is in use. Preferably each sealing rib 80 is a ring shaped member that deforms slightly when it is pressed against an opposite surface. Thus, each sealing rib 80 operates much like O-rings that are well known in the art. However, while an O-ring would work well as a sealing rib with this invention, the preferred sealing ribs 80, unlike a typical O-ring, are not separate pieces but rather are extensions from the applicable surface. This minimizes the time and cost for assembly. The inventor has identified three preferred locations for at least one sealing rib 80. The first location, shown best in FIGS. 8 and 14, is between the cap 100 and the container 30. As shown, at least one sealing rib 80 (two such ribs shown and preferred) extend from a surface of the cap 100. These ribs 80 are received in sealing relationship with the top of the container 30 when the cap 100 is attached to the container 30. The second preferred location for at least one sealing rib 80, shown best in FIGS. 8 and 13, is between the cap 100 and the spike tube 72. As shown, at least one sealing rib 80 extends from an inner surface of the cap 100. This rib 80 is received in sealing relationship with the outer surface of the spike tube 72 when the spike tube 72 is extended through the membrane 66. The third preferred location for at least one sealing rib 80, shown best in FIGS. 8, 11 and 13, is between a top surface 260 of the top portion 110 of the cap 100 and the ring 75 of the head 50. As shown, at least one sealing rib 80 extends from a bottom surface of the ring 75. This rib 80 is received in sealing relationship with the cap 100 when the spike tube 72 is fully extended into the container 30.

Figure 12:
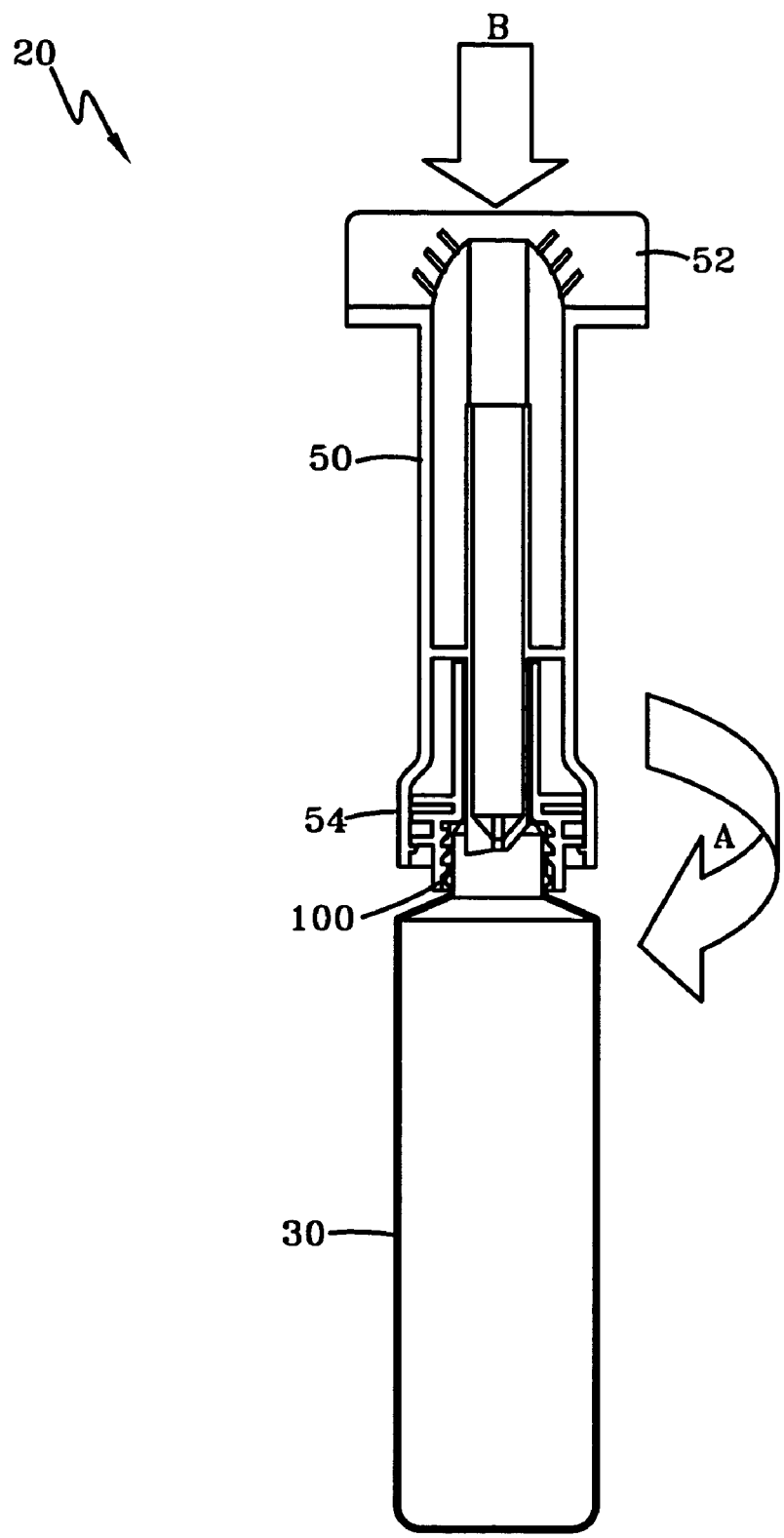
FIG. 12 is a side sectional view of the solution applicator indicating the two steps taken to activate the solution applicator.

With reference now to FIGS. 3–13, the operation of the solution applicator 20 in order to apply a solution will now be described. As shown in FIGS. 12 and 13, overall there are two steps required to break the seal, that is pierce or open the membrane 66, so that the solution may be applied: (A) rotating the head 50 relative to the cap 100; and, (B) axially moving the head 50 relative to the cap 100. More specifically, the user first rotates the head 50 relative to the cap 100 such that the protrusions 56 move within the circumferential channels 202. This rotational movement, in the preferred embodiment, requires the user to move the protrusions 56 over the ramps 222. As noted above, the ramps 222 prevent inadvertent rotational movement of the head 50 relative to the cap 100. Most preferably, this rotational movement is limited by the walls 212. In other words, the protrusions 56 contact the walls 212 and the rotational motion of the head 50 is stopped. This is advantageous because the walls 212 place the protrusions 56 into alignment with the axial channels 204. By alignment it is meant that the protrusions 56 are properly positioned with the axial channels 204 for axial motion. This proper alignment, in the preferred embodiment, can be observed by the user by looking through the slot 255 in the head 50 to observe the surface of the cap 100. When the marking 252 can be seen through the slot 255, the user will know that proper alignment has occurred. Next, the user moves the head 50 axially relative to the cap 100 such that the protrusions 56 move within the axial channels 204. This causes the spike member 58 to extend through the membrane 66 and into the opening 34 in the container 30. This axial movement, in the preferred embodiment, requires the user to move the protrusions 56 over the ramps 220. As noted above, the ramps 220 prevent inadvertent axial movement of the head 50 relative to the cap 100. Finally, the user turns the solution applicator sideways or upside down so that the solution flows through the opening 228 in the cap 100, through the passageway 60 in the head 50 and onto the sponge 64 where the solution may be applied by the user to a patient.

With continuing reference to FIGS. 3–13, it is preferred that the first and second walls 212, 214 extend below third disc 210 as shown in FIG. 6. This prevents the unwanted motion of the head 50 with respect to the cap 100 during application of solution. More specifically, the protrusions 56 are held below the third disc 210 and within the axial channels 204. As a result, the user can control the solution applicator 20 as solution is being applied, sometimes termed scrubbing action, through the sponge 64.

With reference now to FIGS. 5–6, 9 and 12–14, it should be noted that up until now the operation of the solution applicator 20 has only been discussed in terms of use by the end user who will be applying the solution. However, the solution applicator 20 of this invention also provides advantages during the assembly process. As shown in FIG. 6, the first disc 206 has an upper surface with a wall, the previously described fourth wall 218, extending from the upper surface. The first disc 206 also includes another axial ramp 226. This ramp 226 is formed into the edge of the first disc 206 in the same way as the previously described ramp 220. During assembly, the bottom portion 150 of the cap 100 is attached to the first portion 32 of the container 30. The head 50 is then placed onto the cap 100 with the top portion 110 of the cap 100 receiving the spike tube 72 and the bottom portion 54 of the head 50 receiving the mid-portion 200 of the cap 100. At this point, the protrusions 56 rest against the upper surface of the first disc 206 as shown in FIG. 14. The head 50 is then rotated relative to the cap 100 with the protrusions 56 sliding across the upper surface of the first disc 206 to a first position where the protrusion 56 contact the fourth wall 218 which prevents further rotational motion in the same direction. The fourth wall 218 places the protrusions 56 into alignment with an axial ramp 226. The purpose of this ramp 226 is to prevent the inadvertent axial movement of the first protrusion 56 of the head 50 into the first circumferential channel 202. Preferably, an orientation indicator 257 is provided to assist in the assembly of the solution applicator 20. The preferred orientation indicator 257 provides a visual indication that the head 50 is positioned relative to the cap 100 such that the protrusions 56 are in alignment with the axial ramp 226. Though the orientation indicator 257 can be of any type chosen with sound engineering judgment, the preferred orientation indicator 257 includes the previously noted slot 255 in the head and a bar 258 positioned on the cap 100 axially below the ramp 226, as shown in FIG. 5. Most preferably, a separate bar 258 is provided on each side of the cap 100. As the solution applicator 10 is being assembled, the bar 258 can be visually axially oriented with the slot 255 as an indication that the solution indicator 20 is in position to move the head 50 axially with respect to the cap 100. This orientation indicator 12 should increase the output rate of the assembly operation.

The head 50 is then moved axially relative to the cap 100, through the ramp 226, to a second position where the protrusion 56 is received within the circumferential channel 202. This is the condition the end user finds the solution applicator 20 when it is purchased. This end user, when it is desired to apply the solution, then rotates the head 50 relative to the cap 100 to a third position (the position after step A shown in FIGS. 12 and 13) and then to a fourth position as shown in FIG. 13 (the position after step B shown in FIGS. 12 and 13).

The preferred embodiments have been described, hereinabove. It will be apparent to those skilled in the art that the above methods may incorporate changes and modifications without departing from the general scope of this invention. It is intended to include all such modifications and alterations in so far as they come within the scope of the appended claims or the equivalents thereof.

I claim:

1. A solution applicator comprising:
   (1) a container including a first portion defining an opening;
   (2) a head comprising:
      (A) a top portion for use in applying solution;
      (B) a bottom portion;
      (C) at least a first protrusion;
      (D) a spike member; and,
      (E) a passageway for use in communicating solution from the spike member to the top portion of the head; and,
   (3) a cap comprising:
      (A) a top portion that receives the spike member;
      (B) a bottom portion that operatively connects to the first portion of the container; and
      (C) a mid-portion received within the bottom portion of the head, the mid-portion of the cap defining at least a first circumferential channel and at least a first axial channel, the first circumferential channel for use in receiving the first protrusion and permitting the head to rotate relative to the cap, the first axial channel for use in receiving the first protrusion and permitting the head to move axially relative to the cap.

2. The solution applicator of claim 1 wherein the mid-portion of the cap comprises:
   first and second discs positioned substantially perpendicular to a central axis of the top portion of the cap, the first and second discs defining the first circumferential channel.

3. The solution applicator of claim 2 wherein the mid-portion of the cap further comprises:
   first and second walls positioned substantially perpendicular to the first and second discs of the cap, the first and second walls defining the first axial channel.

4. The solution applicator of claim 3 wherein the mid-portion of the cap comprises:
   a third disc positioned substantially parallel to and juxtaposed to the second disc, the third disc defining at least a first axial ramp within the first axial channel, the first axial ramp for use in preventing inadvertent axial movement of the head relative to the cap.

5. The solution applicator of claim 4 wherein the first axial ramp is formed on an outer edge of the third disc between the first and second walls.

6. The solution applicator of claim 4 wherein the first and second walls extend below the third disc.

7. The solution applicator of claim 3 wherein the mid-portion of the cap further comprises:
   a third wall positioned within the first circumferential channel for use in limiting the rotation of the head relative to the cap.

8. The solution applicator of claim 7 wherein the mid-portion of the cap further comprises:
   a fourth wall positioned on the first disc for use in limiting the rotation of the head relative to the cap, the first disc defining at least a first axial ramp for use in preventing inadvertent axial movement of the first protrusion of the head into the first circumferential channel.

9. The solution applicator of claim 2 wherein one of the first and second discs define at least a first circumferential ramp within the first circumferential channel, the first circumferential ramp for use in preventing inadvertent rotation of the head relative to the cap.

10. The solution applicator of claim 9 wherein the first circumferential ramp is positioned at the intersection of the first circumferential channel and the first axial channel.

11. The solution applicator of claim 2 further comprising:
    a wall extending from a top surface of the top disc, the wall, the top disc and the cap forming a solution reservoir.

12. The solution applicator of claim 1 wherein the cap has an opening that extends through the top portion, the mid-portion and the bottom portion, the mid-portion of the cap further comprising:
    a rim portion for use in sealing a membrane against the opening defined by the first portion of the container.

13. The solution applicator of claim 1 wherein the head defines a reservoir, the head further comprising:
    at least a first groove formed on a surface of the top portion of the head, the first groove for use in moving solution from the top portion of the head to the reservoir.

14. The solution applicator of claim 1 wherein the spike member is positioned at an end of a spike tube, the top portion of the cap receiving the spike tube with an interference fit.

15. The solution applicator of claim 1 further comprising:
    an alignment indicator, the alignment indicator comprising a slot in the head and a marking positioned on the cap axially above the first axial channel.

16. The solution applicator of claim 1 further comprising:
    an orientation indicator, the orientation indicator comprising a slot in the head and a bar positioned on the cap axially below the first axial channel.

17. The solution applicator of claim 1 further comprising at least a first sealing rib located between the cap and the container.

18. The solution applicator of claim 1 wherein the spike member is positioned at an end of a spike tube, the solution applicator further comprising at least a first sealing rib located between the cap and the spike tube.

19. The solution applicator of claim 1 further comprising at least a first sealing rib located between a top surface of the top portion of the cap and the head.

20. The solution applicator of claim 1 wherein said container has a membrane over the opening that is puncturable by said spike member.

21. The solution applicator of claim 1 wherein said cap has a membrane that fits over the opening of the container when said cap is attached to the container, said membrane being puncturable.

22. A method of dispensing a solution comprising the steps of:
  I. providing a solution applicator comprising:
    (1) a container including a first portion defining an opening;
    (2) a head comprising:
      (A) a top portion for use in applying solution;
      (B) a bottom portion;
      (C) at least a first protrusion;
      (D) a spike member; and,
      (E) a passageway for use in communicating solution from the spike member to the top portion of the head;
    (3) a cap comprising;
      (A) a top portion that receives the spike member;
      (B) a bottom portion that operatively connects to the first portion of the container; and,
      (C) a mid-portion received within the bottom portion of the head, the mid-portion of the cap defining at least a first circumferential channel and at least a first axial channel;
  II. rotating the head relative to the cap such that first protrusion moves within the first circumferential channel; and
  III. moving the head axially relative to the cap such that the first protrusion moves within the first axial channel and extends the spike member into the opening in the container.

23. The method of claim 22 wherein after the step of rotating the head relative to the cap such that first protrusion moves within the first circumferential channel, the method comprises the step of:
  limiting the rotation of the head such that the first protrusion is in alignment with the first axial channel.

24. The method of claim 22 wherein the step of moving the head axially relative to the cap such that the first protrusion moves within the first axial channel, comprises the step of:
  moving the first protrusion over a ramp that prevents inadvertent axial movement of the head relative to the cap.

25. The method of claim 22 wherein the step of rotating the head relative to the cap such that first protrusion moves within the first circumferential channel, comprises the step of:
  moving the first protrusion over a ramp that prevents inadvertent rotational movement of the head relative to the cap.

26. The method of claim 22 wherein the step of rotating the head relative to the cap such that first protrusion moves within the first circumferential channel, comprises the step of:
  moving the first protrusion until a marking positioned on the cap is lined up with a visual indicator on the head.

27. A method of assembling a solution applicator and dispensing a solution comprising the steps of:
  I. providing a solution applicator comprising:
    (1) a container including a first portion defining an opening;
    (2) a head comprising:
      (A) a top portion for use in applying solution;
      (B) a bottom portion;
      (C) a spike member; and,
      (D) a passageway for use in communicating solution from the spike member to the top portion of the head; and,
    (3) a cap comprising:
      (A) a top portion; and,
      (B) a bottom portion;
  II. attaching the bottom portion of the cap to the first portion of the container;
  III. placing the head onto the cap such that the top portion of the cap receives the spike member and is received within the bottom portion of the head;
  IV. rotating the head relative to the cap to a first position;
  V. moving the head axially relative to the cap to a second position for purposes of assembly;
  VI. rotating the head relative to the cap to a third position;
  VII. moving the head axially relative to the cap to a fourth position for purposes of applying the solution to extend the spike member into the opening in the container.

28. The method of claim 25 wherein prior to the step of attaching the bottom portion of the cap to the first portion of the container, the method comprises the step of:
  attaching a membrane to the cap.

29. The method of claim 25 wherein the step of rotating the head relative to the cap to a first position, comprises the step of:
  rotating the head relative to the cap until an orientation indicator indicates that the solution indicator is in position to move the head axially with respect to the cap.

* * * * *